United States Patent
Chiu

(10) Patent No.: US 10,219,128 B2
(45) Date of Patent: Feb. 26, 2019

(54) WRISTWATCH, WEARABLE DEVICE, EMERGENCY HELP SEEKING METHOD, AND SPEED DIAL METHOD

(71) Applicant: PRINCO CORP., Hsinchu (TW)

(72) Inventor: Pei-liang Chiu, Hsinchu (TW)

(73) Assignee: PRINCO CORP., Hsinchu (TW)

( * ) Notice: Subject to any disclaimer, the term of this patent is extended or adjusted under 35 U.S.C. 154(b) by 0 days.

(21) Appl. No.: 14/988,100

(22) Filed: Jan. 5, 2016

(65) Prior Publication Data

US 2017/0134922 A1    May 11, 2017

(30) Foreign Application Priority Data

Nov. 6, 2015 (TW) .............................. 104136747 A

(51) Int. Cl.
| | |
|---|---|
| *H04W 4/22* | (2009.01) |
| *H04M 1/725* | (2006.01) |
| *H04W 4/14* | (2009.01) |
| *A61B 5/024* | (2006.01) |
| *A61B 5/00* | (2006.01) |
| *G04G 21/04* | (2013.01) |

(Continued)

(52) U.S. Cl.
CPC ........... *H04W 4/22* (2013.01); *A61B 5/02438* (2013.01); *A61B 5/681* (2013.01); *G04G 21/04* (2013.01); *G04G 21/08* (2013.01); *G06F 1/163* (2013.01); *H04M 1/72536* (2013.01); *H04W 4/14* (2013.01)

(58) Field of Classification Search
CPC ..... H04W 40/22; H04W 76/023; H04W 4/22; H04W 76/007
USPC .......................... 455/404.1, 466, 456.6, 445
See application file for complete search history.

(56) References Cited

U.S. PATENT DOCUMENTS

| 5,233,574 A | 8/1993 | Walder et al. |
|---|---|---|
| 7,221,928 B2 * | 5/2007 | Laird ....................... A61B 5/04 |
| | | 340/539.12 |

(Continued)

FOREIGN PATENT DOCUMENTS

| JP | H08287384 A | 11/1996 |
|---|---|---|
| JP | 2002-261982 | 9/2002 |

(Continued)

OTHER PUBLICATIONS

First Office Action dated Jun. 15, 2016, by the Taiwan Intellectual Property Office in related Taiwan Patent Application No. 104136747 (8 pages).

(Continued)

*Primary Examiner* — Cong Tran
(74) *Attorney, Agent, or Firm* — Osha Liang LLP

(57) ABSTRACT

The present invention provides a wristwatch, a wearable device, an emergency help seeking method, and a speed dial method. The present invention can carry out the functions of emergency help seeking and/or speed dial by cooperating a wristwatch or a wearable device putting on a user with the user's mobile terminal. For instance, when the user continuously taps or shakes the wristwatch or wearable device, this action can notify the user's mobile terminal to execute the emergency calling function. According to the number of times the user taps the wristwatch or the wearable device, the mobile terminal can quickly dial, according to the number of times the user taps, a phone number of a contact person corresponding thereto.

30 Claims, 10 Drawing Sheets

(51) Int. Cl.
*G04G 21/08* (2010.01)
*G06F 1/16* (2006.01)

(56) References Cited

U.S. PATENT DOCUMENTS

| | | | |
|---|---|---|---|
| 9,223,296 B2 | 12/2015 | Yang et al. | |
| 2002/0068600 A1* | 6/2002 | Chihara | H04B 1/385 455/557 |
| 2004/0203617 A1* | 10/2004 | Knauerhase | H04L 45/00 455/412.1 |
| 2008/0022089 A1* | 1/2008 | Leedom | H04L 63/068 713/156 |
| 2011/0176490 A1* | 7/2011 | Mehta | A61B 5/0002 370/328 |
| 2013/0017802 A1* | 1/2013 | Adibi | H04W 40/22 455/404.1 |
| 2013/0331058 A1* | 12/2013 | Harvey | H04W 4/22 455/404.2 |
| 2014/0233356 A1 | 8/2014 | Pattikonda | |
| 2014/0347289 A1 | 11/2014 | Suh et al. | |
| 2015/0189056 A1* | 7/2015 | Magi | G06F 1/1652 455/566 |
| 2015/0223705 A1* | 8/2015 | Sadhu | G01S 19/17 600/301 |
| 2015/0269824 A1 | 9/2015 | Zhang | |
| 2015/0296480 A1* | 10/2015 | Kinsey | H04M 19/047 455/41.3 |
| 2015/0358451 A1* | 12/2015 | Cronin | H04B 1/385 455/420 |
| 2016/0110012 A1* | 4/2016 | Yim | G06F 1/1626 345/173 |
| 2016/0205244 A1* | 7/2016 | Dvortsov | H04M 3/42365 455/413 |
| 2016/0282952 A1* | 9/2016 | Slonneger | G06F 3/014 |
| 2016/0354636 A1* | 12/2016 | Jang | A63B 24/0075 |
| 2017/0041205 A1* | 2/2017 | Rangel | H04L 43/065 |

FOREIGN PATENT DOCUMENTS

| | | |
|---|---|---|
| JP | 2003218994 A | 7/2003 |
| JP | 2010096705 A | 4/2010 |
| JP | 2015184254 A | 10/2015 |
| KR | 10-0239089 | 1/2000 |
| KR | 10-2005-0116510 | 12/2005 |
| KR | 10-2010-0035672 | 4/2010 |
| KR | 10-2015-0027876 | 3/2015 |
| KR | 10-1531208 | 6/2015 |
| TW | 200904068 A | 1/2009 |
| TW | M426098 U | 4/2012 |
| TW | M505630 U | 7/2015 |
| TW | 201530503 A | 8/2015 |
| TW | 201531822 A | 8/2015 |
| WO | 2008130511 A1 | 10/2008 |
| WO | 2015141328 A1 | 9/2015 |

OTHER PUBLICATIONS

Office Action issued in corresponding Taiwanese Application No. 104136747 dated Dec. 20, 2016 (8 pages).

Office Action issued in corresponding Japanese Application No. 2016032735 dated Feb. 7, 2017 (3 pages).

* cited by examiner

WRISTWATCH, WEARABLE DEVICE, EMERGENCY HELP SEEKING METHOD, AND SPEED DIAL METHOD

TECHNICAL FIELD OF THE INVENTION

The present invention relates to a device cooperating with a mobile terminal and a method carried out by cooperating with mobile terminal, and more particularly, to a wristwatch, a wearable device, an emergency help seeking method, and a speed dial method.

BACKGROUND OF THE INVENTION

In emergency, a person may use a mobile terminal (e.g., a smart phone and a tablet) to communicate with the others and seek for help. However, when the mobile terminal is happened to be away from the owner, or is distanced apart from the owner and the owner is unable to use the mobile terminal to seek for help in emergency, the owner cannot immediately get the help by using the mobile terminal in such a situation. In addition, the existing mobile terminals have a speed dial function. However, even though the user uses this function, it is required for the user to put through the phone call so as to be able to communicate with the others. It is still inconvenient for the user to use the traditional speed dial function.

SUMMARY OF THE INVENTION

An objective of the present invention is to provide a wristwatch and a wearable device capable of cooperating with a mobile terminal for providing a user with functions of emergency help seeking and/or speed dial.

Another objective of the present invention is to provide an emergency help seeking method such that it is convenient for a user to cooperate a device put on the user with a mobile terminal, thereby carrying out the function of emergency help seeking.

A further objective of the present invention is to provide a speed dial method such that it is convenient for a user to cooperate a device put on the user with a mobile terminal, thereby carrying out the function of speed dial.

To achieve above objectives, an aspect of the present invention provides a wristwatch, having a dial, at least one physical indicator, and a movement, the dial having physical scales disposed thereon, the at least one physical indicator being disposed above the dial, the at least one physical indicator being driven by the movement and cooperating with the physical scales on the dial to show the time, the wristwatch further comprising a functional module disposed therein or on a watch band thereof, the functional module at least comprising: a sensor for sensing an action performed on the wristwatch by a user, the sensor generating a sensing signal when it senses the action performed on the wristwatch by the user; a processor unit coupled to the sensor, the processor unit receiving the sensing signal generated by the sensor and being used to determine whether the action corresponding to the sensing signal is identical to a predetermined action mode, the processor unit generating an instruction when the action corresponding to the sensing signal is identical to the predetermined action mode; and a wireless communication module coupled to the processor unit, the processor unit transmitting the instruction to a mobile terminal by using wireless communication with use of the wireless communication module, and thus the mobile terminal sending out, according to the instruction, a predetermined emergency help message stored in the mobile terminal to one or more contact persons predetermined in the mobile terminal.

Another aspect of the present invention provides a wristwatch, having a dial, at least one physical indicator, and a movement, the dial having physical scales disposed thereon, the at least one physical indicator being disposed above the dial, the at least one physical indicator being driven by the movement and cooperating with the physical scales on the dial to show the time, the wristwatch further comprising a functional module disposed therein or on a watch band thereof, the functional module at least comprising: a sensor for sensing an action performed on the wristwatch by a user, the sensor generating a sensing signal when it senses the action performed on the wristwatch by the user; a processor unit coupled to the sensor, the processor unit receiving the sensing signal generated by the sensor and being used to determine whether the action corresponding to the sensing signal is identical to a predetermined action mode, the processor unit further determining the number of times the action corresponding to the sensing signal is performed during a predetermined period of time when the action corresponding to the sensing signal is identical to the predetermined action mode, the processor unit further generating, according to the predetermined action mode and the number of times, an instruction corresponding the number of times; and a wireless communication module coupled to the processor unit, the processor unit transmitting the instruction to a mobile terminal by using wireless communication with use of the wireless communication module, and thus the mobile terminal dials, according to the instruction, a phone number of a contact person corresponding to the number of times.

A further aspect of the present invention provides a wearable device, at least comprising: a sensor for sensing an action performed on the wearable device by a user, the sensor generating a sensing signal when it senses the action performed on the wearable device by the user; a processor unit coupled to the sensor, the processor unit receiving the sensing signal generated by the sensor and being used to determine whether the action corresponding to the sensing signal is identical to a predetermined action mode, the processor unit generating an instruction when the action corresponding to the sensing signal is identical to the predetermined action mode; and a wireless communication module coupled to the processor unit, the processor unit transmitting the instruction to a mobile terminal by using wireless communication with use of the wireless communication module, and thus the mobile terminal sending out, according to the instruction, a predetermined emergency help message stored in the mobile terminal to one or more contact persons predetermined in the mobile terminal.

A still further aspect of the present invention provides a wearable device, at least comprising: a sensor for sensing an action performed on the wearable device by a user, the sensor generating a sensing signal when it senses the action performed on the wearable device by the user; a processor unit coupled to the sensor, the processor unit receiving the sensing signal generated by the sensor and being used to determine whether the action corresponding to the sensing signal is identical to a predetermined action mode, the processor unit further determining the number of times the action corresponding to the sensing signal is performed during a predetermined period of time when the action corresponding to the sensing signal is identical to the predetermined action mode, the processor unit further generating, according to the predetermined action mode and the number of times, an instruction corresponding the number of times; and a wireless communication module coupled to the processor unit, the processor unit transmitting the instruction to a mobile terminal by using wireless communication with use of the wireless communication module, and thus the mobile terminal dials, according to the instruction, a phone number of a contact person corresponding to the number of times.

A still further aspect of the present invention provides an emergency help seeking method, comprising the steps of: generating, by a device, a sensing signal according to an action performed on the device by a user wearing the device; determining, by the device, whether the action corresponding to the sensing signal is identical to a predetermined action mode; generating an instruction and transmitting it to a mobile terminal when the action corresponding to the sensing signal is identical to the predetermined action mode; and sending out, by the mobile terminal according to the instruction, a predetermined emergency help message stored in the mobile terminal to one or more contact persons predetermined in the mobile terminal.

A still further aspect of the present invention provides a speed dial method, comprising the steps of: generating, by a device, a sensing signal according to an action performed on the device by a user wearing the device; determining, by the device, whether the action corresponding to the sensing signal is identical to a predetermined action mode, and further determining, by the device, the number of times the action corresponding to the sensing signal is performed during a predetermined period of time when the action corresponding to the sensing signal is identical to the predetermined action mode; generating, according to the predetermined action mode and the number of times, an instruction corresponding the number of times, and transmitting the instruction to a mobile terminal; and dialing, by the mobile terminal according to the instruction, a phone number of a contact person corresponding to the number of times.

A still further aspect of the present invention provides a wearable device, comprising: a button or a knob for carrying out an action performed on the wearable device by a user, a signal able to be received by a processor unit being generated when the user operates the button or the knob; the processor unit coupled to the button or the knob, the processor unit receiving the signal generated by the button or the knob and generating, according to the signal generated by the button or the knob, an instruction corresponding to the signal; and a wireless communication module coupled to the processor unit, the processor unit transmitting the instruction to a mobile terminal by using wireless communication with use of the wireless communication module, and thus the mobile terminal sending out, according to the instruction, a predetermined emergency help message stored in the mobile terminal to one or more contact persons predetermined in the mobile terminal.

A still further aspect of the present invention provides a wearable device, comprising: a button or a knob for carrying out an action performed on the wearable device by a user, a signal able to be received by a processor unit being generated when the user operates the button or the knob; the processor unit coupled to the button or the knob, the processor unit receiving the signal generated by the button or the knob and generating, according to the number of times the signal is generated by the button or the knob during a predetermined period of time, an instruction corresponding to the number of times; and a wireless communication module coupled to the processor unit, the processor unit transmitting the instruction to a mobile terminal by using wireless communication with use of the wireless communication module, and thus the mobile terminal dials, according to the instruction, a phone number of a contact person corresponding to the number of times.

A still further aspect of the present invention provides a wearable device, comprising: a display screen for carrying out an action performed on the wearable device by a user, the display screen generating a control signal when the user touches a dedicated menu displayed on the display screen; a processor unit coupled to the display screen, the processor unit receiving the control signal generated by touching the dedicated menu and generating, according to the control signal generated by touching the dedicated menu, an instruction corresponding to the control signal; and a wireless communication module coupled to the processor unit, the processor unit transmitting the instruction to a mobile terminal by using wireless communication with use of the wireless communication module, and thus the mobile terminal sending out, according to the instruction, a predetermined emergency help message stored in the mobile terminal to one or more contact persons predetermined in the mobile terminal.

A still further aspect of the present invention provides a wearable device, comprising: a display screen for carrying out an action performed on the wearable device by a user, the display screen generating a control signal when the user touches a dedicated menu displayed on the display screen; a processor unit coupled to the display screen, the processor unit receiving the control signal generated by touching the dedicated menu and generating, according to the received control signal, an instruction corresponding to the control signal; and a wireless communication module coupled to the processor unit, the processor unit transmitting the instruction to a mobile terminal by using wireless communication with use of the wireless communication module, and thus the mobile terminal dials, according to the instruction, a phone number of a corresponding contact person.

A still further aspect of the present invention provides an emergency help seeking method, comprising the steps of: generating an instruction by a device according to an action performed on the device by a user wearing the device, and transmitting the instruction to a mobile terminal; and sending out, by the mobile terminal according to the instruction, a predetermined emergency help message stored in the mobile terminal to one or more contact persons predetermined in the mobile terminal.

A still further aspect of the present invention provides a speed dial method, comprising the steps of: generating a specific control signal by a device according to an action performed on the device by a user wearing the device; generating, by the device according to the specific control signal, an instruction corresponding to the specific control signal, and transmitting the instruction to a mobile terminal; and dialing, by the mobile terminal according to the instruction, a phone number of a contact person corresponding to the instruction.

The present invention can carry out the functions of emergency help seeking and/or speed dial by cooperating a wristwatch or a wearable device putting on a user with the user's mobile terminal. For instance, the user continuously taps or shakes the wristwatch or wearable device and this action can notify, by using wireless communication between the user's mobile terminal and the wristwatch (or the wearable device) the user's mobile terminal to execute the emergency calling function, sending out an emergency help message to a predetermined contact person. In another aspect, according to the number of times (e.g., one/two/three times) the user taps the wristwatch or the wearable device, the mobile terminal can quickly dial, according to the number of times the user taps, a phone number of a contact person corresponding thereto. The concepts of the present invention are applicable to traditional wristwatches, and to wearable devices as well.

DETAILED DESCRIPTION OF THE INVENTION

To make the objectives, technical schemes, and technical effects of the present invention more clearly and definitely, the present invention will be described in details below by using embodiments in conjunction with the appending drawings. It should be understood that the specific embodiments described herein are merely for explaining the present invention, and as used herein, the term "embodiment" refers to an instance, an example, or an illustration but is not intended to limit the present invention. In addition, the articles "a" and "an" as used in the specification and the appended claims should generally be construed to mean "one or more" unless specified otherwise or clear from the context to be directed to a singular form. Also, in the appending drawings, the components having similar or the same structure or function are indicated by the same reference number.

The present invention relates to a wristwatch, which cooperates with a mobile terminal such as a smart phone and a tablet, for providing a user with functions of emergency help seeking and/or speed dial. As to the emergency help seeking, the user can perform an action on the wristwatch (e.g., continuous shaking the wristwatch or tapping the surface of the wristwatch) such that emergency help message stored in the mobile terminal can be transmitted to one or more predetermined contact persons via wireless communication between the wristwatch and the mobile terminal. As to the speed dial, the mobile terminal can quickly dial, according to an action performed by the user on the wristwatch (e.g., the number of times tapping the surface of the wristwatch), a phone number corresponding to a predetermined contact person. The following paragraphs are described with an application of the present invention as an example, that is, quartz watches. However, for a person skilled in the art, it can be understood that the concepts of the present invention are also applicable to traditional mechanical watches, electronic watches, or other types of traditional watches, and can also be applied to smart watches or the likes, such as wearable devices.

Figure 1:
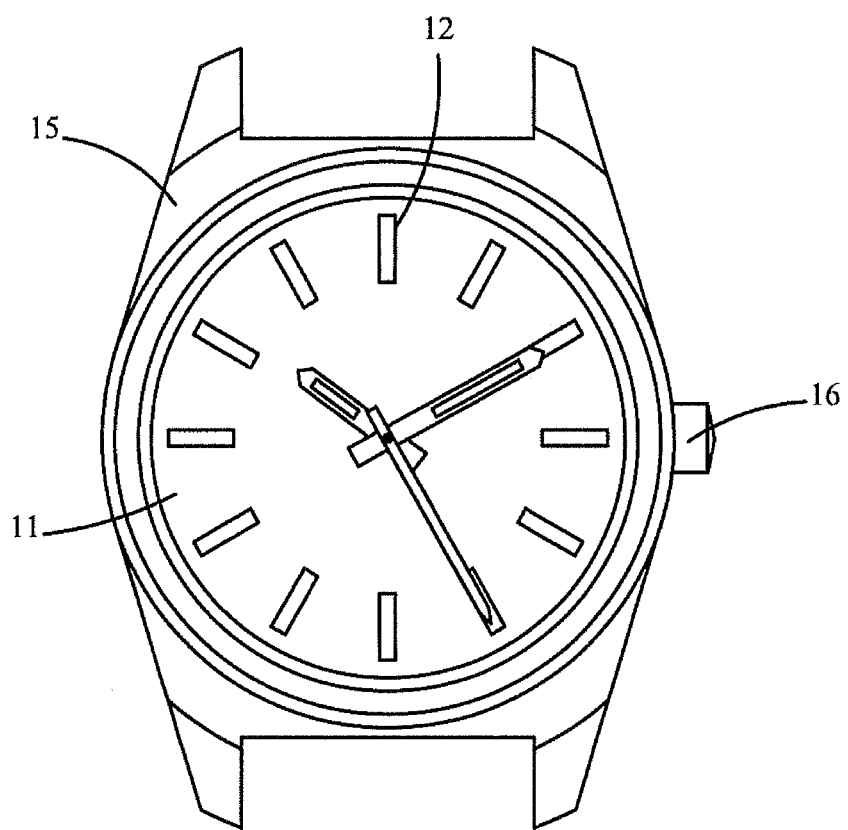
FIG. 1 is a top view of a wristwatch in accordance with an embodiment of the present invention.
Figure 2:
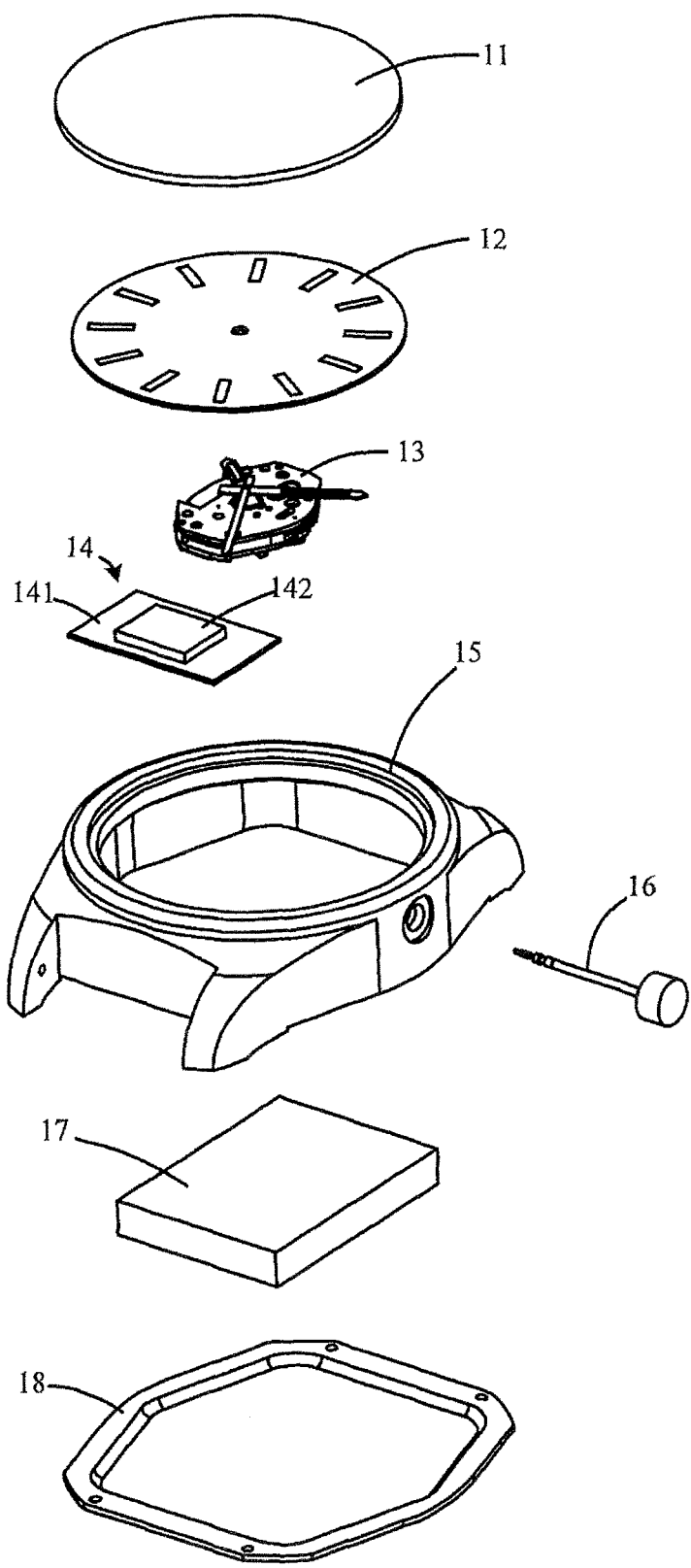
FIG. 2 is an exploded view of the wristwatch shown in FIG. 1.
Figure 3:
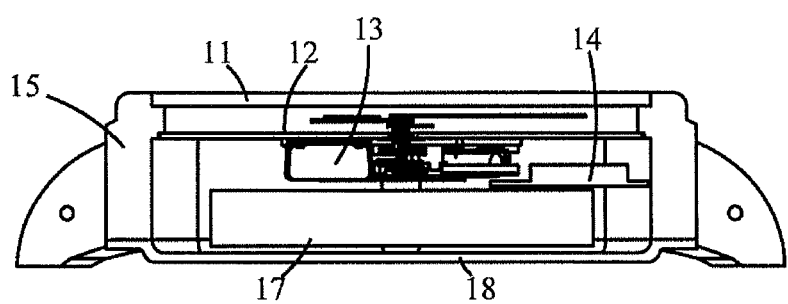
FIG. 3 is a sectional view of the wristwatch shown in FIG. 2.

Please refer to FIG. 1, FIG. 2, and FIG. 3. FIG. 1 is a top view of a wristwatch in accordance with an embodiment of the present invention. FIG. 2 is an exploded view of the wristwatch shown in FIG. 1. FIG. 3 is a sectional view of the wristwatch shown in FIG. 2. The wristwatch in accordance with the embodiment of the present invention comprises a glass 11, a dial 12, a movement 13, a functional module 14, a watch case 15, a crown 16, a battery 17, and a bottom case 18. The glass 11 is made of a transparent material (i.e., glass material). The dial 12 has physical scales (e.g., one o'clock to twelve o'clock) disposed thereon. Indicators (e.g., physical hands including a hour hand, a minute hand, and a second hand) are arranged above the dial 12. The indicators are driven by the movement 13 and cooperates with the scales on the dial 12 to show the time. Through the transparent glass 11, a user can perceive the position information (i.e., time information) indicated by the indicators. The watch case 15 and the bottom case 18 are used to protect the mechanical structures and/or electronic devices inside the wristwatch. The watch case 15, the bottom case 18, and the dial 12 (or the glass 11) construct an accommodating space for accommodating the movement 13, the functional module 14 and the battery 17. Also, the wristwatch has the crown 16 disposed at the lateral side thereof. The user can adjust the correct time or set an alarm by turning a knob on the crown 16. The battery 17 can provide the power required by the movement 13 and/or the functional module 14. The functional module 14 cooperates with the mobile terminal for providing the user with functions of emergency help seeking and/or speed dial. The functional module 14 can also be deployed on a watch strap.

As can be seen from FIG. 1 to FIG. 3 of the present invention, even though there may have a slight difference in design, the functions of the glass 11, the dial 12, the movement 13, the watch case 15, the crown 16, the battery 17, and the bottom case 18 are similar to that of a traditional wristwatch, especially corresponding to the framework of a quartz watch. However, distinguished from the conventional skills, the wristwatch in accordance with the embodiment of the present invention comprises the functional module 14. That is to say, remaining room in a traditional quartz watch can be reused to equip such a functional module 14 or the quartz watch can be improved to accommodate such a functional module 14, thereby carrying out the functions of emergency help seeking and/or speed dial in conjunction with the mobile terminal. In such a manner, the traditional wristwatch becomes intelligent. Similarly, the functional module 14 of the present invention can also be deployed in a mechanical watch, an electronic watch, or other types of traditional watches such that they have intelligent functions. Such a concept is similar to the example of quartz watch, and is not detailed herein.

In the embodiment of the present invention, the battery 17 can supply power to the movement 13 and the functional module 14. That is, the movement 13 and the functional module 14 (and the other electronic devices inside the wristwatch) can concurrently use the electric power stored in the battery 17. In other embodiments, the movement 13 and the functional module 14 may have individual batteries and power supply systems. That is, the movement 13 and the functional module 14 can be supplied by different batteries.

Figure 4:
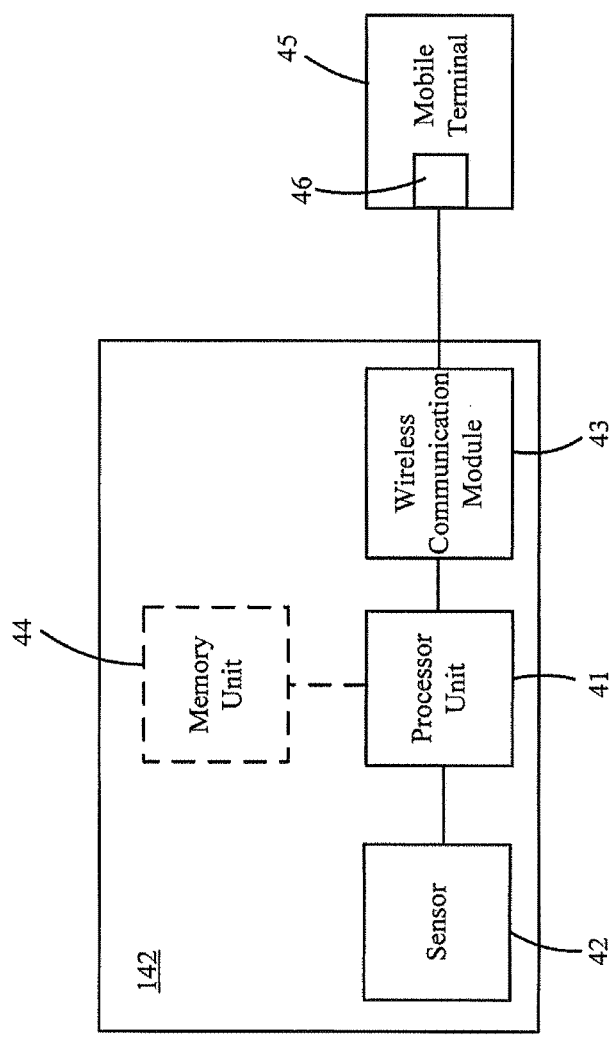
FIG. 4 is a schematic diagram showing a communication framework of a functional module and a mobile terminal in accordance with the present invention.

As shown in FIG. 2, the functional module 14 comprises an electronical connecting substrate 141 and a packaging body 142 disposed on the electronical connecting substrate 141. FIG. 4 is a schematic diagram showing a communication framework of a functional module 14 and a mobile terminal 45 in accordance with the present invention. Please refer to FIG. 4 in conjunction with FIGS. 1 to 3. The packaging body 142 of the functional module 14 of the present invention has a processor unit 41, a sensor 42, and a wireless communication module 43 deployed therein. The processor unit 41, the sensor 42, and the wireless communication module 43 can be packaged into a monolithic packaging structure, such as a SIP (System in Package) structure, on the electronical connecting substrate 141, and can also be individually packaged or any two of them are integrated into one package, and then electronic signal transmission is accomplished by layout structure on a same or different electronical connecting substrates. The electronical connecting substrate 141 can be implemented by a flexible multi-layer substrate or a rigid one, which has a plurality of metal layers and a plurality of dielectric layers. The metal layers are distributed between the respective dielectric layers and are used to transmit electronic signals. The material of the dielectric layers may be polyimide and the dielectric layers may be formed by spin coating.

The functional module 14 may also comprise a memory unit 44 for storing the data required by the processor unit 41. Also, the memory unit 44 can be integrated into the processor unit 41. The mobile terminal 45 has a wireless signal transceiver 46 for receiving and transmitting wireless signals. For example, the wireless signal transceiver 46 may be implemented by a bluetooth transceiver or a NFC (Near Field Communication) transceiver.

The wireless communication module 43 of the functional module 14 is a communication module (such as a bluetooth communication module or a NFC communication module) able to communication with the wireless signal transceiver 46 of the mobile terminal 45. The sensor 42 of the functional module 14 is a sensor able to sense the action (for example, that makes a displacement or an angular displacement of the sensor 42) performed by the user on the wristwatch and output an electronic signal according to that. For example, the sensor 42 might be a vibration transducer for sensing vibration or the like that a user made on it. Such an action may be achieved by continuous shaking or tapping, for example. The sensor 42 can also be an acceleration sensor (e.g., an accelerometer) or an angular speed sensor (e.g., a gyroscope). The sensor 42 may also be implemented by a three-axis inertial sensor, a six-axis inertial sensor (including a three-axis gyroscope and a three-axis accelerometer), or a high-level inertial sensor such as a nine-axis inertial sensor (including a three-axis gyroscope, a three-axis accelerometer, and a three-axis magnetic field sensor).

Please refer to FIG. 4 in conjunction with FIGS. 1 to 3. In the aspect of emergency help seeking provided by the wristwatch of the present invention, when the sensor 42 senses an action performed by a user on the wristwatch, the sensor 42 generates a sensing signal and transmits the sensing signal to the processor unit 41. The processor unit 41 determines whether an action mode corresponding to the sensing signal is identical to a first predetermined action mode (e.g., continuously shaking or continuously tapping). When the action mode is identical to the first predetermined action mode, the processor unit 41 generates a first instruction and transmits the first instruction to the mobile terminal 45 by using wireless communication (e.g., bluetooth communication and NFC communication) between the wireless communication module 43 of the wristwatch and the wireless signal transceiver 46 of the mobile terminal 45. When the mobile terminal 45 receives the first instruction, the mobile terminal 45 transmits, according to the first instruction, an emergency help message to one or more predetermined contact persons. The emergency help message can be a predetermined text message or e-mail content, or a predetermined recorded audio content or a conversation using a communication software or a social network site. The first predetermined action mode can also be rotation, that is, rotation of the wristwatch. Preferably, after the mobile terminal 45 sends out the emergency help message, the mobile terminal 45 further transmits an acknowledgement signal to the processor unit 41 by using the wireless communication between the wireless signal transceiver 46 of the mobile terminal 45 and the wireless communication module 43 of the wristwatch. Based on the acknowledgement signal, the processor unit 41 sends out a prompt message and order a vibrator to vibrate (e.g., a long vibration movement), so as to notify the user that the mobile terminal 45 has sent out the emergency help message. The prompt message can also be an audio prompt message. In another embodiment, the wristwatch (or a wearable device) may comprise a button or a knob. The knob can also be a rotatable small plate. When the user operates the button or the knob, that is, an action is performed by the user on the wristwatch (or the wearable device), a signal is generated correspondingly and is then received by the processor unit 41. This embodiment is different from the afore-mentioned approach of motion detecting. This embodiment is to notify, by operating the button or the knob on the wristwatch (or the wearable device), the mobile terminal 45 to send out the emergency help message. In a further embodiment, the wristwatch (or a wearable device) may comprise a display screen. The difference between the present embodiment and the afore-mentioned embodiments is that in the present embodiment, the user can notify the mobile terminal 45 to send out the emergency help message, by touching a certain item of a dedicated menu displayed on the display screen (i.e., touch control).

Figure 5A:
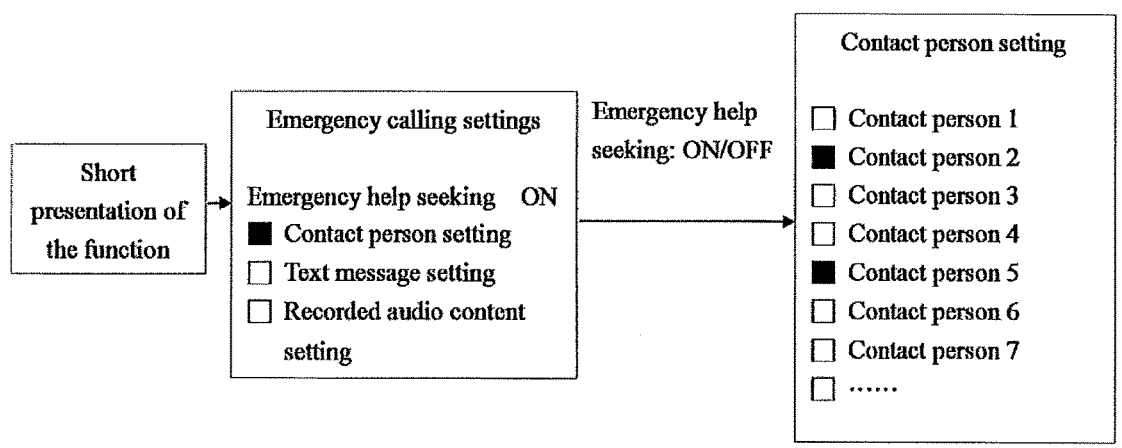
FIG. 5A is a schematic diagram showing contact person setting of an application program installed in a mobile terminal in accordance with an emergency help seeking function of the present invention.
Figure 5B:
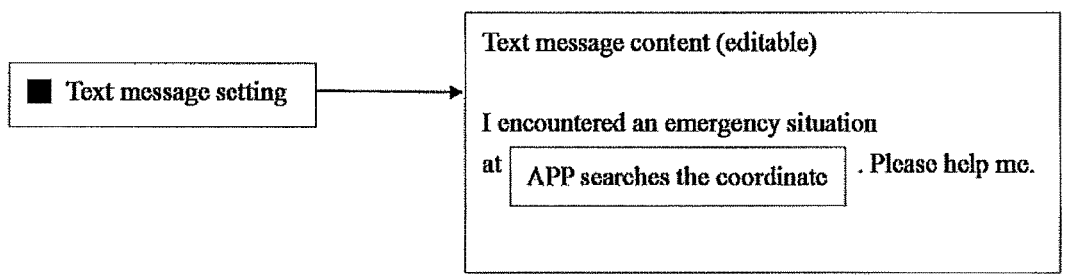
FIG. 5B is a schematic diagram showing text message setting of the application program installed in the mobile terminal in accordance with the emergency help seeking function of the present invention.
Figure 5C:
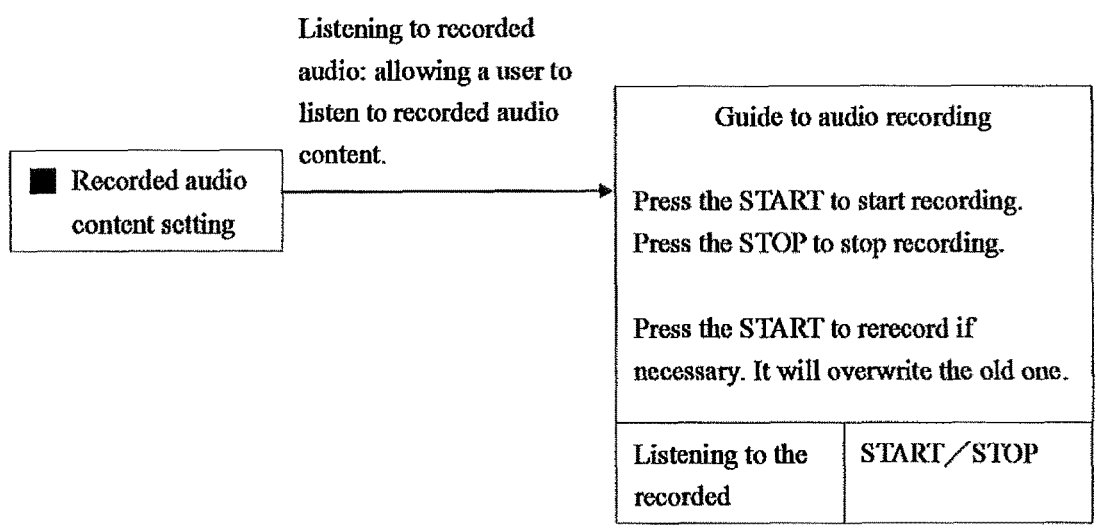
FIG. 5C is a schematic diagram showing recorded audio content setting of the application program installed in the mobile terminal in accordance with the emergency help seeking function of the present invention.

Referring to FIG. 5A to FIG. 5C, these are schematic diagrams showing an interface of an application program (APP) installed in the mobile terminal 45 correspondingly having the function of emergency help seeking. As shown in FIG. 5A, the APP of the mobile terminal 45 comprises a setting interface relates to the function of emergency help seeking. Contact persons preassigned to receive the emergency help message, content of a text message, and recorded audio content can be preset through the setting interface. As shown in FIG. 5A, after "contact person setting" is selected, it can go to a next menu to select the contact persons preassigned to receive the emergency help message. As shown in FIG. 5S, after "text message setting" is selected, it can go to a next menu to input the content of text message associated with the emergency help message, and the mobile terminal 45 can automatically capture a satellite positioning coordinate (for example, using GPS (Global Positioning System)) or latitude and longitude coordinates of a current location and can automatically insert such a coordinate into the content of text message. In such a manner, the contact person receiving the emergency help message can know where the emergency happens. Referring to FIG. 5C, after "recorded audio content setting" is selected, it can go to a next menu to listen an old audio content or rerecord a new audio content. In emergency help seeking, the recorded audio content can be transmitted to one or more predetermined or preassigned contact persons together with the text message.

Please refer to FIG. 4 in conjunction with FIGS. 1 to 3. In the aspect of speed dial provided by the wristwatch of the present invention, when the sensor 42 senses an action performed by a user on the wristwatch, the sensor 42 generates a sensing signal and transmits the sensing signal to the processor unit 41. The processor unit 41 determines whether an action mode corresponding to the sensing signal is identical to a second predetermined action mode (e.g., tapping). When they are identical to each other, the processor unit 41 further determines the number of times the action is performed (e.g., the number of tapping motions) during a predetermined period of time, and generates, according to the second predetermined action mode and the number of times the action is performed, a second instruction corresponding to the number of times the action is performed and transmits the second instruction to the mobile terminal 45 by using wireless communication (e.g., bluetooth communication and NFC communication) between the wireless communication module 43 of the wristwatch and the wireless signal transceiver 46 of the mobile terminal 45. When the mobile terminal 45 receives the second instruction, the mobile terminal 45 quickly dial, according to the second instruction, a phone number of a corresponding contact person. The second predetermined action mode can also be rotation. The number of times the action corresponding to the sensing signal is performed during the predetermined period of time is just the number of rotating motions. The second predetermined action mode can also be shaking. The number of times the action corresponding to the sensing signal is performed during the predetermined period of time is just the number of shaking motions. Preferably, the second instruction generated by the processor unit 41 may comprise an instruction for ordering the mobile terminal 45 to quickly dial a phone number, and a flag. The mobile terminal 45 records the relationship between the flag and the contact person. For instance, the processor unit 41 will envelop flag "1" in the second instruction when the tapping is performed one time. The processor unit 41 will envelop flag "2" in the second instruction when the tapping is performed two times. The processor unit 41 will envelop flag "3" in the second instruction when the tapping is performed three times. The mobile terminal 45 stores information of contact persons corresponding to the respective flags "1", "2", and "3". Accordingly, the mobile terminal 45 can call a corresponding contact person based on the flag. In addition, preferably, after the mobile terminal 45 executes the speed dial function and determines that the other end is connected (i.e., the other end is answering the phone call), the mobile terminal 45 may further transmit an acknowledgement signal to the processor unit 41 by using the wireless communication between the wireless signal transceiver 46 of the mobile terminal 45 and the wireless communication module 43 of the wristwatch. Based on the acknowledgement signal, the processor unit 41 sends out a prompt message and order a vibrator to vibrate (e.g., a long vibration movement), so as to notify the user that the call has been put through. The prompt message can also be an audio prompt message. In such a manner, by using the speed dial function provided in the present invention, the user can pick up the cell phone for conversation after the call is put through, without necessary to pick up the cell phone and dial and wait for putting through the phone call. This reduces the time waiting for putting through the phone call. In another embodiment, the wristwatch (or a wearable device) may comprise a button or a knob. The knob can also be a rotatable small plate. When the user operates the button or the knob, that is, an action is performed by the user on the wristwatch (or the wearable device), a signal is generated correspondingly and is then received by the processor unit 41. This embodiment is different from the afore-mentioned approach of motion detecting. This embodiment is to notify, by operating the button or the knob on the wristwatch (or the wearable device) and using the number of times the operation is performed, the mobile terminal 45 to execute the speed dial function and call a contact person corresponding the number of times the operation is performed. In a further embodiment, the wristwatch (or a wearable device) may comprise a display screen. The difference between the present embodiment and the afore-mentioned embodiments is that in the present embodiment, the user can notify the mobile terminal 45 to execute the speed dial function, by touching a certain item of a dedicated menu displayed on the display screen (i.e., touch control).

Figure 6:
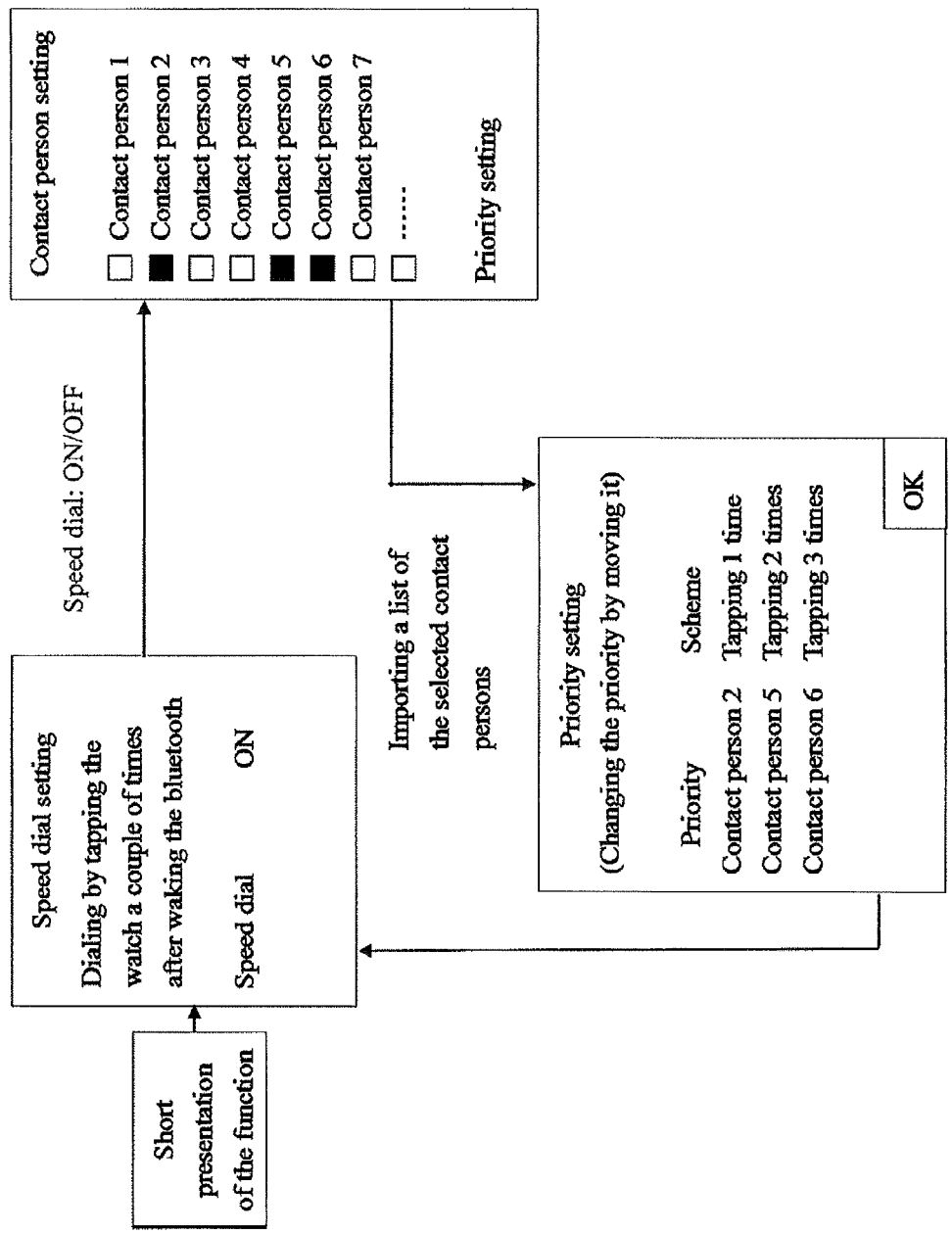
FIG. 6 is a schematic diagram showing settings of an application program installed in a mobile terminal in accordance with a speed dial function of the present invention.

Please refer to FIG. 6, which is a schematic diagram showing an interface of an application program (APP) installed in the mobile terminal 45 correspondingly having the function of speed dial. The functional module 14 of the wristwatch can be put in a standby mode for saving the power. When the speed dial function is to be executed, the wristwatch may be changed from the standby mode to an operable normal mode and be triggered on by moving it back and forth, shaking it, or performing another specific action. As shown in FIG. 6, the function of speed dial can be triggered on or off by changing the settings of the APP installed in the mobile terminal 45. Also, by use of "contact person setting", contact persons can be selected to bind to the speed dial function. After the contact persons are selected, the item "priority setting" may be pressed to enter a priority setting menu. In this menu, the user can change the priority of the selected contact persons by sliding up and down on the screen. As shown in FIG. 6, a contact person corresponding to the action of "tapping the glass one time" in the speed dial function can be determined; a contact person corresponding to the action of "tapping the glass two times" in the speed dial function can be determined; a contact person corresponding to the action of "tapping the glass three times" in the speed dial function can be determined. In this way, the setting of contact persons binding to the speed dial function is accomplished.

As described above, the above embodiments are illustrated by taking the traditional quartz watch and its improvements as an example. However, by the above descriptions, it can be understood for a person skilled in the art that the functional module 14 of the wristwatch of the present invention can also be deployed in a wearable device such as a smart watch, an intelligent band, a life recording band, and a health recording band, thereby having the same functions of emergency help seeking and speed dial as the present invention. Therefore, the present invention is also applicable to the wearable devices but is not limited to traditional wristwatches. Further, the processor unit 41, the sensor 42, and the wireless communication module 43 of the functional module 14 of the present invention can be integrated into the wearable device. That is, the present invention can use the processor unit, the sensor, and the wireless communication module inherently existing in the wearable device, to carry out the functions of emergency help seeking and speed dial described in the present invention. Therefore, the wearable devices using the present invention to carry out the functions of emergency help seeking and speed dial are still within the scope of the present invention.

Figure 7:
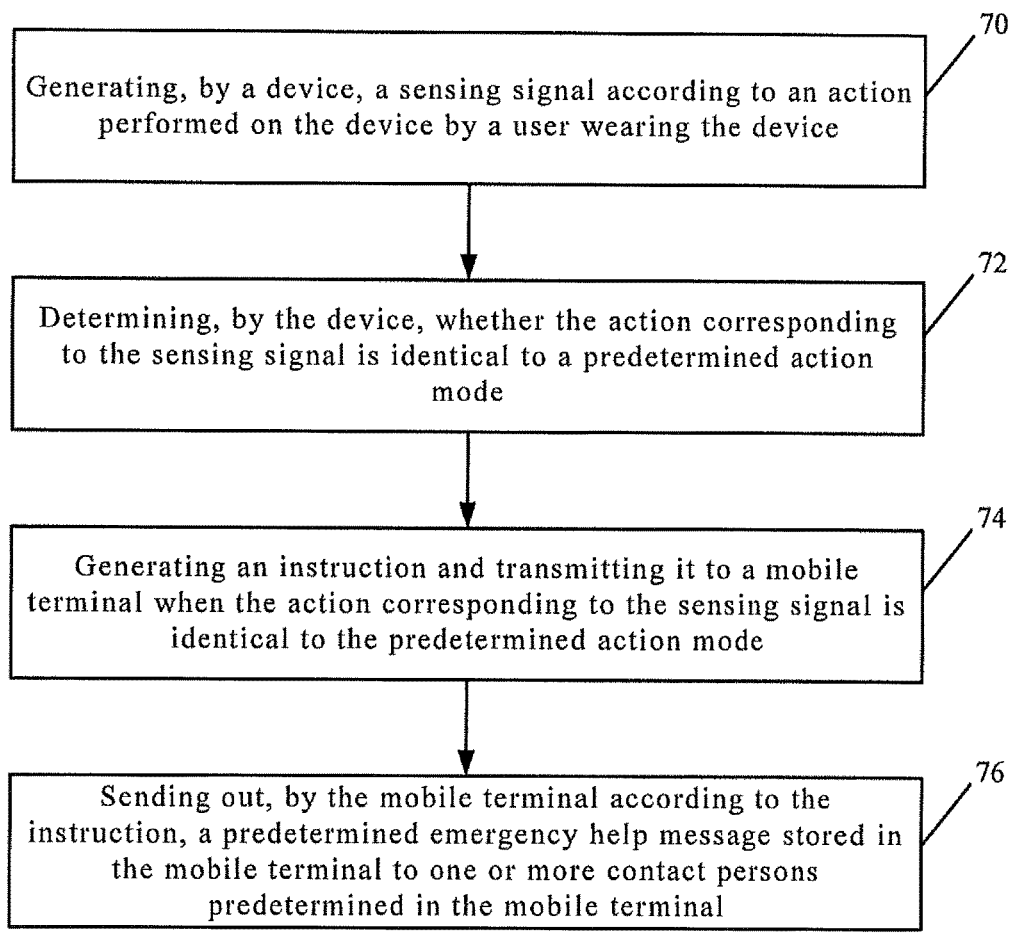
FIG. 7 is a flow chart of an emergency help seeking method in accordance with the present invention.

Please refer to FIG. 7 in conjunction with FIGS. 1 to 4. Respective processes of an emergency help seeking method provided in the present invention will be described below with reference to above contents.

In Step 70, a device generates a sensing signal according to an action performed on the device by a user wearing the device.

In Step 72, the devices determines whether the action corresponding to the sensing signal is identical to a first predetermined action mode (e.g., continuously shaking or continuously tapping). As described above, the first predetermined action mode can also be rotation, that is, rotation of the wristwatch.

In Step 74, a first instruction is generated and is transmitted to a mobile terminal when the action corresponding to the sensing signal is identical to the first predetermined action mode.

In Step 76, the mobile terminal sends out, according to the first instruction, a predetermined emergency help message stored in the mobile terminal to one or more contact persons predetermined in the mobile terminal.

Figure 8:
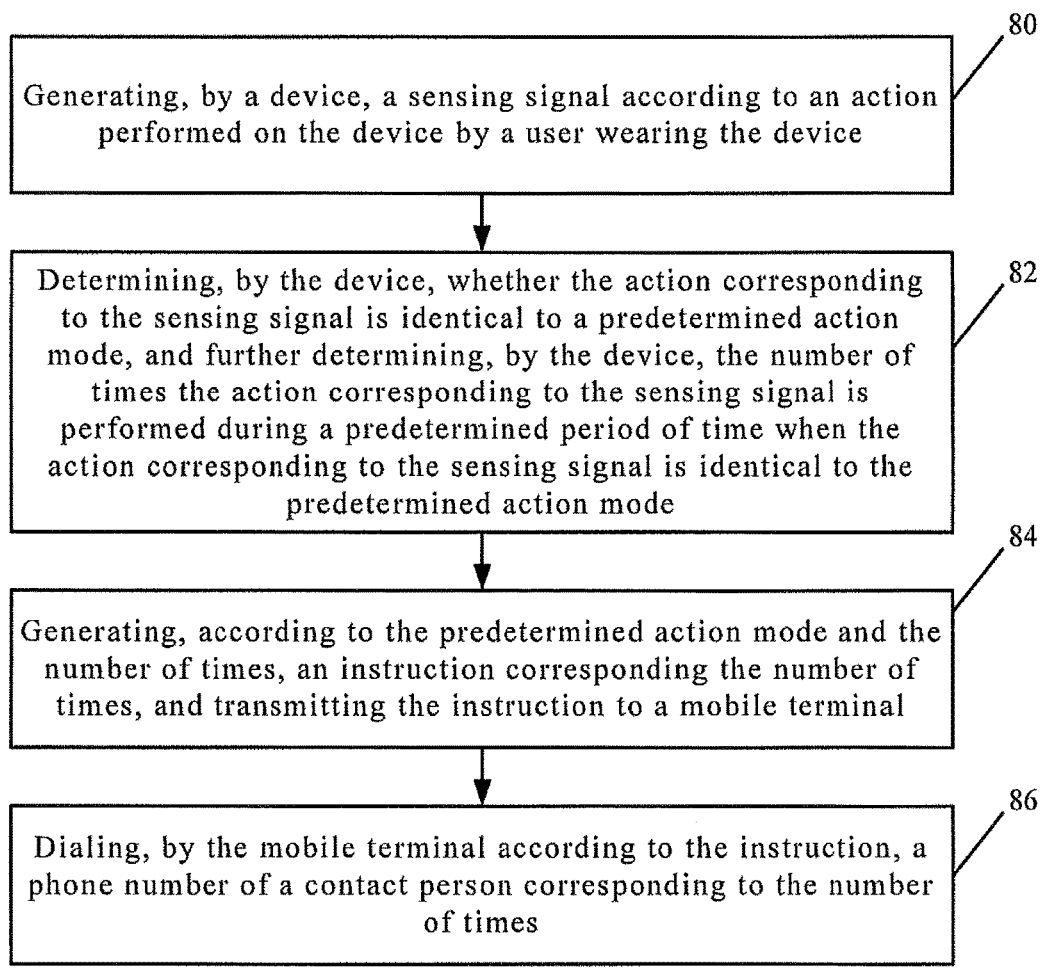
FIG. 8 is a flow chart of a speed dial method in accordance with the present invention.

Please refer to FIG. 8 in conjunction with FIGS. 1 to 4. Respective processes of a speed dial method provided in the present invention will be described below with reference to above contents.

In Step 80, a device generates a sensing signal according to an action performed on the device by a user wearing the device.

In Step 82, the device determines whether the action corresponding to the sensing signal is identical to a second predetermined action mode (e.g., tapping). The device further determines the number of times the action corresponding to the sensing signal is performed during a predetermined period of time when the action corresponding to the sensing signal is identical to the second predetermined action mode.

The second predetermined action mode can also be rotation. The number of times the action corresponding to the sensing signal is performed during the predetermined period of time is just the number of rotating motions. The second predetermined action mode can also be shaking. The number of times the action corresponding to the sensing signal is performed during the predetermined period of time is just the number of shaking motions.

In Step 84, a second instruction corresponding the number of times is generated, according to the second predetermined action mode and the number of times, and is transmitted to a mobile terminal.

In Step 86, the mobile terminal quickly dials, according to the second instruction, a phone number of a contact person corresponding to the number of times.

The present invention can carry out the functions of emergency help seeking and/or speed dial by cooperating a wristwatch or a wearable device putting on a user with the user's mobile terminal. For instance, the user continuously taps or shakes the wristwatch or wearable device and this action can notify, by using wireless communication between the user's mobile terminal and the wristwatch (or the wearable device) the user's mobile terminal to execute the emergency calling function, sending out an emergency help message to a predetermined contact person. In another aspect, according to the number of times (e.g., one/two/three times) the user taps the wristwatch or the wearable device, the mobile terminal can quickly dial, according to the number of times the user taps, a phone number of a contact person corresponding thereto. The concepts of the present invention are applicable to traditional wristwatches, and to wearable devices as well.

While the preferred embodiments of the present invention have been illustrated and described in detail, various modifications and alterations can be made by persons skilled in this art. The embodiment of the present invention is therefore described in an illustrative but not restrictive sense. It is intended that the present invention should not be limited to the particular forms as illustrated, and that all modifications and alterations which maintain the spirit and realm of the present invention are within the scope as defined in the appended claims.

What is claimed is:

1. A wristwatch, having a dial, at least one physical indicator, and a movement, the dial having physical scales disposed thereon, the at least one physical indicator being disposed above the dial, the at least one physical indicator being driven by the movement and cooperating with the physical scales on the dial to show the time, the wristwatch further comprising a functional module disposed therein or on a watch band thereof, the functional module at least comprising:

a sensor for sensing an action performed on the wristwatch by a user, the sensor generating a sensing signal when it senses the action performed on the wristwatch by the user;

a processor unit coupled to the sensor, the processor unit receiving the sensing signal generated by the sensor and being used to determine whether the action corresponding to the sensing signal is identical to a predetermined action mode, the processor unit generating an instruction when the action corresponding to the sensing signal is identical to the predetermined action mode; and a wireless communication module coupled to the processor unit, the processor unit transmitting the instruction to a mobile terminal by using wireless communication with use of the wireless communication module, and thus the mobile terminal sending out, according to the instruction, a predetermined emergency help message stored in the mobile terminal to one or more contact persons predetermined in the mobile terminal.

2. The wristwatch according to claim 1, wherein the predetermined action mode comprises shaking.

3. The wristwatch according to claim 1, wherein the predetermined action mode comprises rotating.

4. The wristwatch according to claim 1, wherein the predetermined action mode comprises continuous tapping.

5. The wristwatch according to claim 1, wherein after the mobile terminal sends out the predetermined emergency help message, the mobile terminal further transmits an acknowledgement signal to the processor unit of the wristwatch, and the processor unit sends out a prompt message to notify the user after receiving the acknowledgement signal.

6. The wristwatch according to claim 5, wherein the prompt message sent out by the processor unit is a vibration prompt.

7. The wristwatch according to claim 5, wherein the prompt message sent out by the processor unit is an audio prompt.

8. The wristwatch according to claim 1, wherein the predetermined emergency help message sent out by the mobile terminal comprises text message content and/or e-mail content.

9. The wristwatch according to claim 8, wherein the text message content and/or the e-mail content comprise location information of the mobile terminal, and the location information of the mobile terminal comprises a coordinate obtained by using a satellite positioning system.

10. The wristwatch according to claim 1, wherein the predetermined emergency help message sent out by the mobile terminal comprises recorded audio content.

11. A wristwatch, having a dial, at least one physical indicator, and a movement, the dial having physical scales disposed thereon, the at least one physical indicator being disposed above the dial, the at least one physical indicator being driven by the movement and cooperating with the physical scales on the dial to show the time, the wristwatch further comprising a functional module disposed therein or on a watch band thereof, the functional module at least comprising:
  a sensor for sensing an action performed on the wristwatch by a user, the sensor generating a sensing signal when it senses the action performed on the wristwatch by the user;
  a processor unit coupled to the sensor, the processor unit receiving the sensing signal generated by the sensor and being used to determine whether the action corresponding to the sensing signal is identical to a predetermined action mode, the processor unit further determining the number of times the action corresponding to the sensing signal is performed during a predetermined period of time when the action corresponding to the sensing signal is identical to the predetermined action mode, the processor unit further generating, according to the predetermined action mode and the number of times, an instruction corresponding the number of times; and
  a wireless communication module coupled to the processor unit, the processor unit transmitting the instruction to a mobile terminal by using wireless communication with use of the wireless communication module, and thus the mobile terminal dials, according to the instruction, a phone number of a contact person corresponding to the number of times.

12. The wristwatch according to claim 11, wherein the predetermined action mode comprises tapping, and the number of times the action corresponding to the sensing signal is performed during the predetermined period of time is the number of tapping motions.

13. The wristwatch according to claim 11, wherein the predetermined action mode comprises rotating, and the number of times the action corresponding to the sensing signal is performed during the predetermined period of time is the number of rotating motions.

14. The wristwatch according to claim 11, wherein the predetermined action mode comprises shaking, and the number of times the action corresponding to the sensing signal is performed during the predetermined period of time is the number of shaking motions.

15. The wristwatch according to claim 11, wherein the instruction generated by the processor unit comprises an instruction for executing speed dial and a flag corresponding to the number of times the action corresponding to the sensing signal is performed, and the mobile terminal dials the phone number of the contact person corresponding to the flag.

16. The wristwatch according to claim 11, wherein after the mobile terminal executes speed dial and determines that the contact person is answering the call, the mobile terminal transmits an acknowledgement signal to the processor unit of the wristwatch, and the processor unit sends out a prompt message to notify the user after receiving the acknowledgement signal.

17. The wristwatch according to claim 16, wherein the prompt message sent out by the processor unit is a vibration prompt.

18. The wristwatch according to claim 16, wherein the prompt message sent out by the processor unit is an audio prompt.

19. A wearable device, at least comprising:
  a sensor for sensing an action performed on the wearable device by a user, the sensor generating a sensing signal when it senses the action performed on the wearable device by the user;
  a processor unit coupled to the sensor, the processor unit receiving the sensing signal generated by the sensor and being used to determine whether the action corresponding to the sensing signal is identical to a predetermined action mode, the processor unit generating an instruction when the action corresponding to the sensing signal is identical to the predetermined action mode; and
  a wireless communication module coupled to the processor unit, the processor unit transmitting the instruction to a mobile terminal by using wireless communication with use of the wireless communication module, and thus the mobile terminal sending out, according to the instruction, a predetermined emergency help message stored in the mobile terminal to one or more contact persons predetermined in the mobile terminal,
  wherein the predetermined action mode comprises continuous tapping.

20. A wearable device, at least comprising:
  a sensor for sensing an action performed on the wearable device by a user, the sensor generating a sensing signal when it senses the action performed on the wearable device by the user;
  a processor unit coupled to the sensor, the processor unit receiving the sensing signal generated by the sensor and being used to determine whether the action corresponding to the sensing signal is identical to a predetermined action mode, the processor unit further determining the number of times the action corresponding to the sensing signal is performed during a predetermined period of time when the action corresponding to the sensing signal is identical to the predetermined action mode, the processor unit further generating, according to the predetermined action mode and the number of times, an instruction corresponding the number of times; and
  a wireless communication module coupled to the processor unit, the processor unit transmitting the instruction to a mobile terminal by using wireless communication with use of the wireless communication module, and thus the mobile terminal dials, according to the instruction, a phone number of a contact person corresponding to the number of times.

21. An emergency help seeking method, comprising the steps of:
  generating, by a device, a sensing signal according to an action performed on the device by a user wearing the device;
  determining, by the device, whether the action corresponding to the sensing signal is identical to a predetermined action mode;

generating an instruction and transmitting it to a mobile terminal when the action corresponding to the sensing signal is identical to the predetermined action mode; and sending out, by the mobile terminal according to the instruction, a predetermined emergency help message stored in the mobile terminal to one or more contact persons predetermined in the mobile terminal, wherein the predetermined action mode comprises continuous tapping.

22. A speed dial method, comprising the steps of:

generating, by a device, a sensing signal according to an action performed on the device by a user wearing the device;

determining, by the device, whether the action corresponding to the sensing signal is identical to a predetermined action mode, and further determining, by the device, the number of times the action corresponding to the sensing signal is performed during a predetermined period of time when the action corresponding to the sensing signal is identical to the predetermined action mode;

generating, according to the predetermined action mode and the number of times, an instruction corresponding the number of times, and transmitting the instruction to a mobile terminal; and dialing, by the mobile terminal according to the instruction, a phone number of a contact person corresponding to the number of times.

23. A wearable device, comprising:

a button or a knob for carrying out an action performed on the wearable device by a user, a signal able to be received by a processor unit being generated when the user operates the button or the knob;

the processor unit coupled to the button or the knob, the processor unit receiving the signal generated by the button or the knob and generating, according to the signal generated by the button or the knob, an instruction corresponding to the signal; and a wireless communication module coupled to the processor unit, the processor unit transmitting the instruction to a mobile terminal by using wireless communication with use of the wireless communication module, and thus the mobile terminal sending out, according to the instruction, a predetermined emergency help message stored in the mobile terminal to one or more contact persons predetermined in the mobile terminal, wherein the predetermined action mode comprises continuous tapping.

24. A wearable device, comprising:

a button or a knob for carrying out an action performed on the wearable device by a user, a signal able to be received by a processor unit being generated when the user operates the button or the knob;

the processor unit coupled to the button or the knob, the processor unit receiving the signal generated by the button or the knob and generating, according to the number of times the signal is generated by the button or the knob during a predetermined period of time, an instruction corresponding to the number of times; and a wireless communication module coupled to the processor unit, the processor unit transmitting the instruction to a mobile terminal by using wireless communication with use of the wireless communication module, and thus the mobile terminal dials, according to the instruction, a phone number of a contact person corresponding to the number of times.

25. A wearable device, comprising:

a display screen for carrying out an action performed on the wearable device by a user, the display screen generating a control signal when the user touches a dedicated menu displayed on the display screen;

a processor unit coupled to the display screen, the processor unit receiving the control signal generated by touching the dedicated menu and generating, according to the control signal generated by touching the dedicated menu, an instruction corresponding to the control signal; and a wireless communication module coupled to the processor unit, the processor unit transmitting the instruction to a mobile terminal by using wireless communication with use of the wireless communication module, and thus the mobile tenninal sending out, according to the instruction, a predetermined emergency help message stored in the mobile terminal to one or more contact persons predetermined in the mobile terminal.

26. A wearable device, comprising:

a display screen for carrying out an action performed on the wearable device by a user, the display screen generating a control signal when the user touches a dedicated menu displayed on the display screen;

a processor unit coupled to the display screen, the processor unit receiving the control signal generated by touching the dedicated menu and generating, according to the received control signal, an instruction corresponding to the control signal; and a wireless communication module coupled to the processor unit, the processor unit transmitting the instruction to a mobile terminal by using wireless communication with use of the wireless communication module, and thus the mobile terminal dials, according to the instruction, a phone number of a corresponding contact person.

27. An emergency help seeking method, comprising the steps of:

generating an instruction by a device according to an action performed on the device by a user wearing the device, and transmitting the instruction to a mobile terminal; and sending out, by the mobile terminal according to the instruction, a predetermined emergency help message stored in the mobile terminal to one or more contact persons predetermined in the mobile terminal, wherein the action performed on the device by a user wearing the device comprises continuous tapping.

28. A speed dial method, comprising the steps of:

generating a specific control signal by a device according to an action performed on the device by a user wearing the device;

generating, by the device according to the specific control signal, an instruction corresponding to the specific control signal, and transmitting the instruction to a mobile terminal; and dialing, by the mobile terminal according to the instruction, a phone number of a contact person corresponding to the instruction.

29. A wearable device, at least comprising:

a sensor for sensing an action performed on the wearable device by a user, the sensor generating a sensing signal when it senses the action performed on the wearable device by the user;

a processor unit coupled to the sensor, the processor unit receiving the sensing signal generated by the sensor and being used to determine whether the action corresponding to the sensing signal is identical to a predetermined action mode, the processor unit generating an instruction when the action corresponding to the sensing signal is identical to the predetermined action mode; and
a wireless communication module coupled to the processor unit, the processor unit transmitting the instruction to a mobile terminal by using wireless communication with use of the wireless communication module, and thus the mobile terminal sending out, according to the instruction, a predetermined emergency help message stored in the mobile terminal to one or more contact persons predetermined in the mobile terminal,
wherein the predetermined action mode comprises shaking.

30. A wearable device, at least comprising:
a sensor for sensing an action performed on the wearable device by a user, the sensor generating a sensing signal when it senses the action performed on the wearable device by the user;
a processor unit coupled to the sensor, the processor unit receiving the sensing signal generated by the sensor and being used to determine whether the action corresponding to the sensing signal is identical to a predetermined action mode, the processor unit generating an instruction when the action corresponding to the sensing signal is identical to the predetermined action mode; and
a wireless communication module coupled to the processor unite the processor unit transmitting the instruction to a mobile terminal by using wireless communication with use of the wireless communication module, and thus the mobile terminal sending out, according to the instruction, a predetermined emergency help message stored in the mobile terminal to one or more contact persons predetermined in the mobile terminal,
wherein the predetermined action mode comprises rotating.

* * * * *